(12) United States Patent
Ouchi

(10) Patent No.: US 6,612,982 B1  
(45) Date of Patent: *Sep. 2, 2003

(54) FULLY-SWALLOWABLE ENDOSCOPIC SYSTEM

(75) Inventor: Teruo Ouchi, Saitama (JP)

(73) Assignee: Pentax Corporation, Tokyo (JP)

( * ) Notice: Subject to any disclaimer, the term of this patent is extended or adjusted under 35 U.S.C. 154(b) by 191 days.

This patent is subject to a terminal disclaimer.

(21) Appl. No.: 09/588,468

(22) Filed: Jun. 6, 2000

(30) Foreign Application Priority Data

Jun. 7, 1999  (JP) .......................... 11-160027

(51) Int. Cl.$^7$ ................................. A61B 1/00
(52) U.S. Cl. .................. 600/139; 600/109; 600/130; 600/141; 600/151
(58) Field of Search ................. 600/101, 109, 600/128, 130, 136, 141, 139, 143, 151, 152; 348/65, 68, 71, 74

(56) References Cited

U.S. PATENT DOCUMENTS

| | | | | |
|---|---|---|---|---|
| 4,633,304 A | * | 12/1986 | Nagasaki | 600/109 |
| 5,398,670 A | * | 3/1995 | Ortiz et al. | 600/109 |
| 5,595,565 A | * | 1/1997 | Treat et al. | 600/101 |
| 5,604,531 A | * | 2/1997 | Iddan et al. | 600/109 |
| 5,662,587 A | * | 9/1997 | Grundfest et al. | 600/114 |
| 6,162,171 A | * | 12/2000 | Ng et al. | 600/101 |
| 6,240,312 B1 | * | 5/2001 | Alfano et al. | 600/476 |

FOREIGN PATENT DOCUMENTS

| | | | |
|---|---|---|---|
| GB | WO 98/11816 | * | 3/1998 |
| JP | 64-4450 | | 1/1989 |
| JP | 64-76822 | | 3/1989 |
| JP | 3-9705 | | 1/1991 |
| JP | 4-144533 | | 5/1992 |
| JP | 6-114064 | | 4/1994 |
| JP | 7-111985 | | 5/1995 |

* cited by examiner

*Primary Examiner*—John P. Leubecker  
(74) *Attorney, Agent, or Firm*—Greenblum & Bernstein, P.L.C.

(57) ABSTRACT

A fully-swallowable endoscopic system includes a rod-shaped endoscope body which can be swallowed entirely by a patient to be examined so as to be placed in a body cavity, at least part of the rod-shaped endoscope body includes a bendable portion which is bendable along a curve of the body cavity; and an external device provided separately from the rod-shaped endoscope body having no mechanical connection with the rod-shaped endoscope body. The rod-shaped endoscope body is provided therein with a light emitter, an observing system, a transmitter for transmitting a radio wave which carries an image formed by the observing system, and a power supplying device. The external device includes a receiver for receiving the radio wave which carries the image.

18 Claims, 8 Drawing Sheets

FULLY-SWALLOWABLE ENDOSCOPIC SYSTEM

BACKGROUND OF THE INVENTION

1. Field of the Invention

The present invention relates to a fully-swallowable endoscopic system which can relieve a patient to be examined from pain, even if the endoscope is retained in the patient's body for a long time.

2. Description of the Related Art

In an endoscopy examination, in general, an insertion portion connected to an operation portion is introduced into a patient's body through his or her mouth to observe a target inner part of the body. The insertion portion of the endoscope must be sometimes inserted and retained in the body for a long time to observe the progress of a diseased part within the body or to obtain and/or record somatoscopic information of a patient under ordinary every-day living conditions. However, the insertion and retainment of the endoscope in the body through the patient's mouth causes the patient to suffer from significant pain.

To relieve pain from the patient, it is known to use a capsule type endoscope which is provided at an intermediate portion of a flexible continuous member, as disclosed in Japanese Unexamined Patent Publication No. 64-76822. A patient to be examined swallows a soft ball formed at a tip end of the flexible continuous member the night before the day of examination, so that the soft ball is discharged from the patient's anus the next day. An operator pulls or moves the tip end and the tail end of the flexible continuous member to thereby move or guide the capsule connected to the intermediate portion of the flexible continuous member.

In the capsule type of endoscope described above, the pain that the patient suffers can be eased in comparison with conventional endoscopes. However, the patient must always carry the flexible continuous member whose one end extends out of his or her mouth for more than 12 hours. Consequently, it is impossible for the patient to take a meal or speak. Under these circumstances, no substantial pain relieving effect can be expected. Moreover, it is generally difficult to control the position of the endoscope when in the form of a capsule.

SUMMARY OF THE INVENTION

It is an object of the present invention to provide a fully-swallowable endoscopic system which can relieve a patient to be examined from pain.

To achieve the object mentioned above, according to the present invention, a fully-swallowable endoscopic system is provided, which includes a rod-shaped endoscope body which can be swallowed entirely by a patient to be examined so as to be placed in a body cavity, at least part of the rod-shaped endoscope body including a bendable portion which is bendable along a curve of the body cavity; and an external device provided separately from the rod-shaped endoscope body having no mechanical connection with the rod-shaped endoscope body. The rod-shaped endoscope body is provided therein with a light emitter, an observing system, a transmitter for transmitting a radio wave which carries an image formed by the observing system, and a power supplying device. The external device includes a receiver for receiving the radio wave which carries the image.

Preferably, the bendable portion includes a bending portion which can be radio-controlled to bend by an operation of the external device, and a flexible portion which bends when an external force is applied to the flexible portion. The rod-shaped endoscope body is provided therein with a radio-controlled driving device which receives a radio operational signal transmitted from the external device to bend the bending portion in accordance with the radio operational signal, and the external device includes an operational portion which is operated to transmit the radio operational signal to the radio-controlle d driving device.

In an embodiment, the rod-shaped endoscope body further includes a hard portion, wherein the hard portion and the bendable portion are arranged in that order from one of the opposite ends of the rod-shaped endoscope body in a longitudinal direction thereof, the light emitter and the observing system being positioned in the hard portion.

In another embodiment, the rod-shaped endoscope body further includes a hard portion, and the hard portion, the bending portion and the flexible portion are arranged in that order from one of the opposite ends of the rod-shaped endoscope body in a longitudinal direction thereof, the light emitter and the observing system being positioned in the hard portion.

Preferably, the radio-controlled driving device includes a plurality of drive wires made of a shape memory alloy, and a selective-heating device which selectively heats the plurality of drive wires to bend the bending portion.

The power supplying device can be in the form of a built-in battery.

In an embodiment, the external device includes a microwave transmitter for transmitting a microwave to the rod-shaped endoscope body, and the power supplying device converts the microwave into electrical current to supply the electrical current to the rod-shaped endoscope body.

Preferably, the observing system includes an objective optical system and a CCD image sensor.

Preferably, the external device includes a monitor which visually indicates the image.

According to another aspect of the present invention, a fully-swallowable endoscopic system is provided, which includes a rod-shaped endoscope body having a hard portion, a bending portion and a flexible portion which are arranged in that order, and a radio controller for manipulating the bending portion to bend by radio-control. The rod-shaped endoscope body is provided therein with a light emitter for illuminating a target inner portion of a living body, an image pick-up device for taking an image of the target inner portion illuminated by the light emitter, and a transmitter for transmitting a radio wave which carries the image taken by the image pick-up device.

Preferably, the radio controller includes a monitor and a receiver, for receiving the radio wave, wherein the image is indicated on the monitor.

In an embodiment, the radio controller further includes a second transmitter for transmitting a microwave to the rod-shaped endoscope body, and wherein the rod-shaped endoscope body is provided therein with a power supplying device which receives the microwave to convert the microwave into electrical current which is to be used as a power source of the rod-shaped endoscope body.

The present disclosure relates to subject matter contained in Japanese Patent Application No. 11-160027 (filed on Jun. 7, 1999) which is expressly incorporated herein by reference in its entirety.

BRIEF DESCRIPTION OF THE DRAWINGS

The invention will be discussed below in detail with reference to the drawings, in which.

DESCRIPTION OF THE PREFERRED EMBODIMENTS

Figure 1:
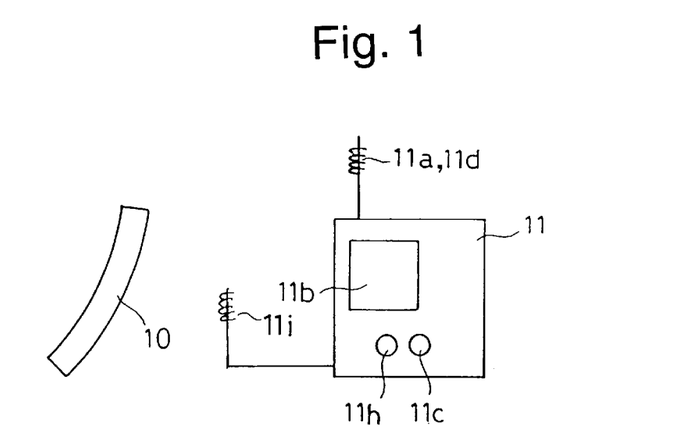
FIG. 1 is a schematic view of an embodiment of an endoscopic system comprising a fully-swallowable endoscope body and an external device, according to the present invention.

FIG. 1 shows an embodiment of a fully-swallowable endoscopic system which includes a rod-shaped endoscope body 10 and an external device 11. A patient to be examined swallows the rod-shaped endoscope body 10 before an endoscopic examination is performed with the endoscope 10. The external device 11 functions as a wireless controller (radio controller) and a power supply for the endoscope 10.

FIGS. 2, 3, 10, 11, 16 and 17 show the first embodiment of the rod-shaped endoscope body 10. The rod-shaped endoscope body 10 is provided with a hard portion (unbendable portion) 12, a bending portion 13 and a flexible portion 14, in this order from the front end (the left end as viewed in FIG. 2). The bending portion 13 and the flexible portion 14 constitute a bendable portion. The rod-shaped endoscope body 10 is entirely covered by an elastic covering 27 (see FIG. 16) whose outer surface is smooth and well-slidable. The hard portion 12 is made of a hard material (e.g., a hard plastic) which is not macroscopically deformable. The flexible portion 14 is designed to be bendable along the shape of a digestive tract when it is inserted in the body cavity.

Figure 2:
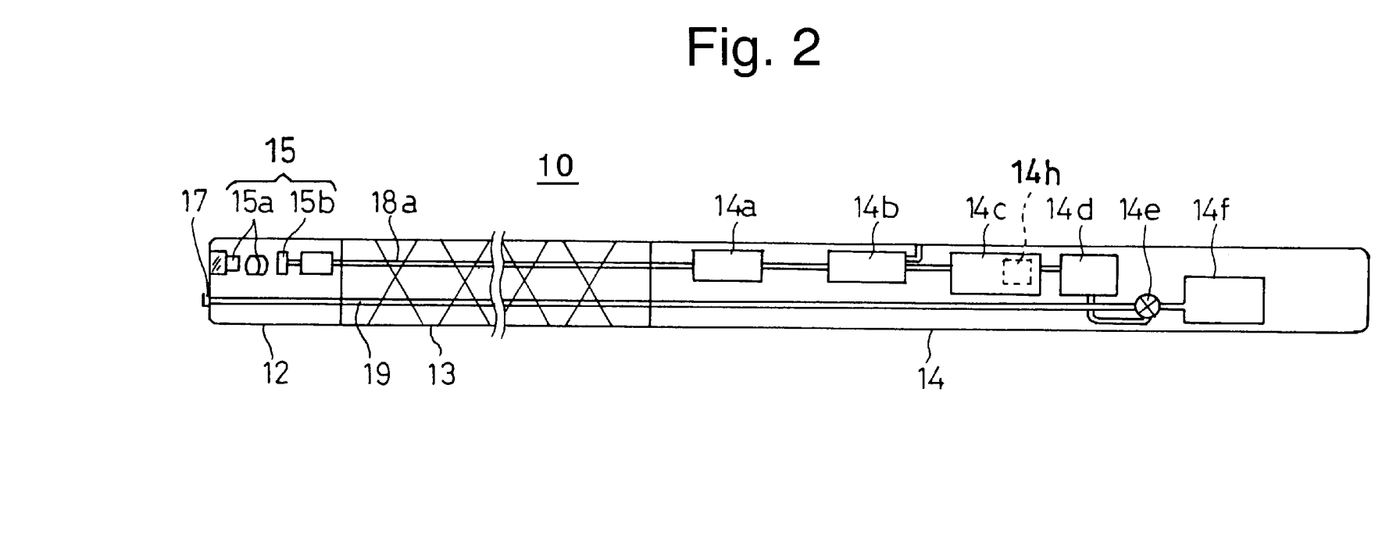
FIG. 2 is a schematic cross sectional view of the first embodiment of the rod-shaped endoscope body, according to the present invention.
Figure 3:
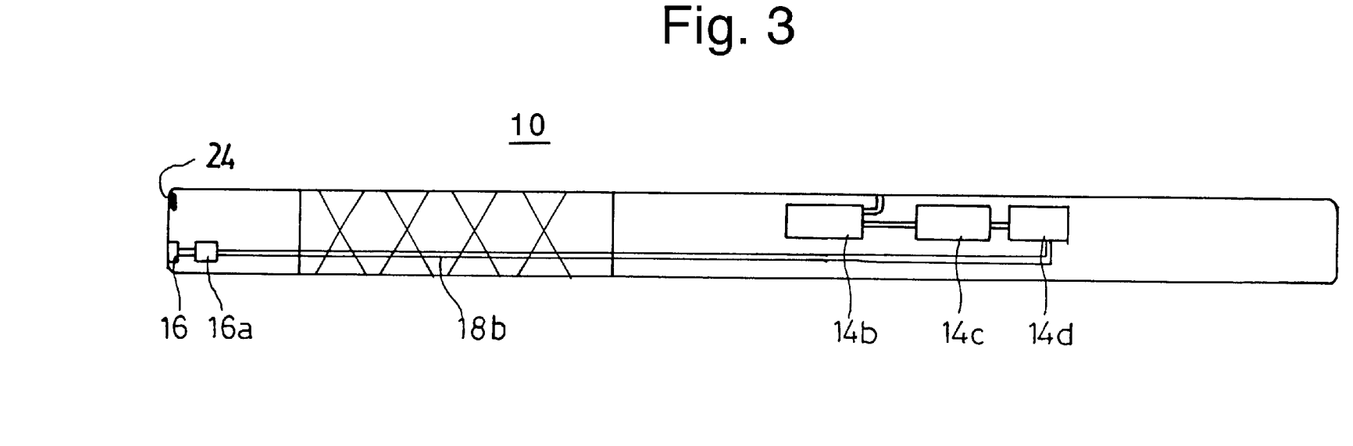
FIG. 3 is a schematic cross sectional view of the rod-shaped endoscope body shown in FIG. 2, taken along a different plane.

The hard portion 12 is provided therein with an observing system 15, an illumination window 16 and an air supply port 17. The observing system 15 includes an objective optical system 15a and a CCD image sensor 15b. The flexible portion 14 is provided therein with an amplifier circuit 14a, a transmitter/receiver device 14b, a power supplying device 14c, a control circuit 14d, a compressed air tank 14f and a microwave receiver 14h. The CCD image sensor 15b is connected to the amplifier circuit 14a via a signal line 18a which extends within the bending portion 13. The amplifier circuit 14a is connected to the transmitter/receiver-device 14b, which is positioned in the flexible portion 14. The hard portion 12 is provided therein with an LED (light emitter) 16a which is secured to the illumination window 16. The LED 16a is connected to the control circuit 14d via a signal line 18b which extends within the bending portion 13.

The air supply port 17 is connected to the front end of an air supply tube 19 which extends within the hard portion 12, the bending portion 13 and the flexible portion 14. The rear end of the air supply tube 19 is connected to the compressed air tank 14f. The compressed air tank 14f is provided with a valve 14e which is controlled to open or shut by the control circuit 14d. The power supplying device 14c is connected to the transmitter/receiver device 14b and the control circuit 14d. The power supplying device 14c converts a microwave: received by the microwave receiver 14h into electrical current to supply the same to the transmitter/receiver device 14b and the control circuit 14d. The microwave received by the microwave receiver 14h is transmitted from the external device 11.

Figure 16:
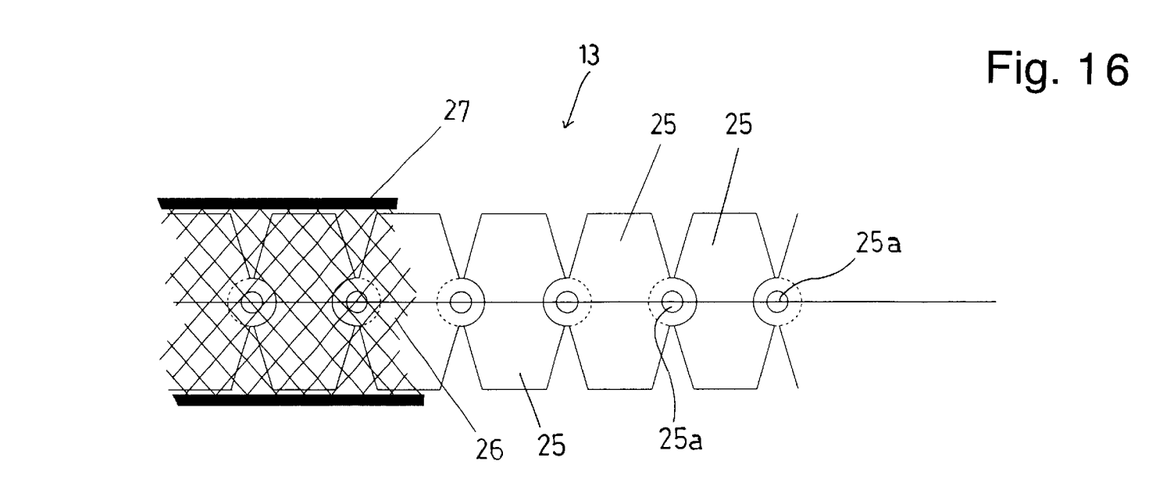
FIG. 16 is a schematic side view of part of the first embodiment of the bending portion, with parts omitted for clarity, in the case where the bending portion is designed to be bendable in a single plane.

FIG. 16 shows part of the first embodiment of the bending portion 13 in the case where the bending portion 13 is designed to be bendable in a single plane. The first embodiment of the bending portion 13 is provided with an articulated series of ring joints 25. Adjacent ring joints 25 are connected with each other by a shaft 25a so that each of the adjacent ring joints 25 can rotate about the shaft 25a. All the shafts 25a are parallel to one another so as to lie in a common plane. The articulated series of ring joints 25 having such a structure is covered by a steel wired tube 26. This steel wired tube 26 is covered by the aforementioned elastic covering 27. The bending portion 13 is designed to bend with respect to the flexible portion 14, and to be more flexible and bendable than the flexible portion 14.

Figure 10:
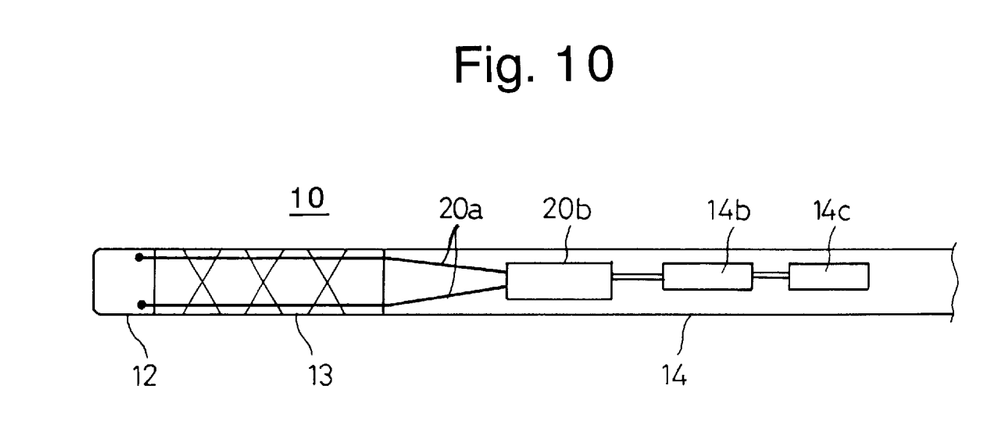
FIG. 10 is a schematic cross sectional view of part of the rod-shaped endoscope body shown in FIGS. 2 and 3, showing the structure of a bending portion.
Figure 11:
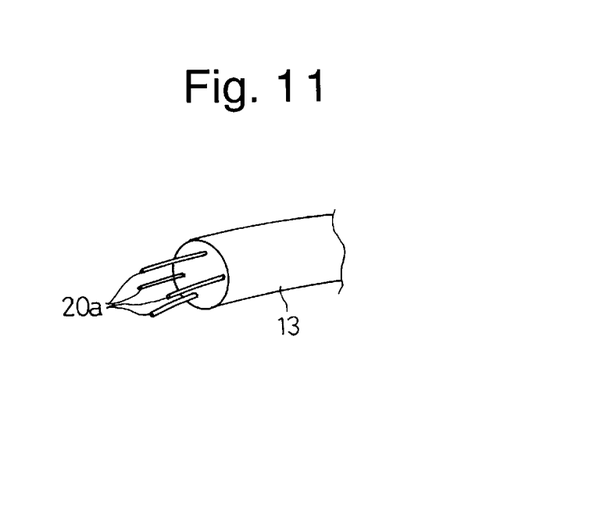
FIG. 11 is an explanatory view of part of the second embodiment of the bending portion of the rod-shaped endoscope body, showing an arrangement of the bendable drive wires provided in the bending portion.

The rod-shaped endoscope body 10 is provided therein with a plurality of bendable drive wires (two wires in the first embodiment of the bending portion 13) 20a which extend within the bending portion 13 and the flexible portion 14 (see FIG. 10). Each drive wire 20a is made of a shape memory alloy (SMA) which bends when supplied with electrical current to be heated thereby. The rod-shaped endoscope body 10 is further provided therein with a selective-heating device 20b which is connected to the transmitter/receiver device 14b. The drive wires 20a, the selective heating device 20b, and the transmitting/receiving device 14b constitute a radio-controlled driving device. The front ends of the drive wires 20a are each secured to the hard portion 12, while the rear ends of the same are each secured to the selective-heating device 20b.

The two drive wires 20a are diametrically arranged at opposite sides of the axis of the cylindrical bending portion 13. The selective-heating device 20b is a circuit which selectively supplies electrical current to the two drive wires 20a to heat the same in accordance with control signals output from the transmitter/receiver device 14b, which makes it possible to bend the bending portion 13 in a plane in which the two drive wires 20a lie.

Figure 17:
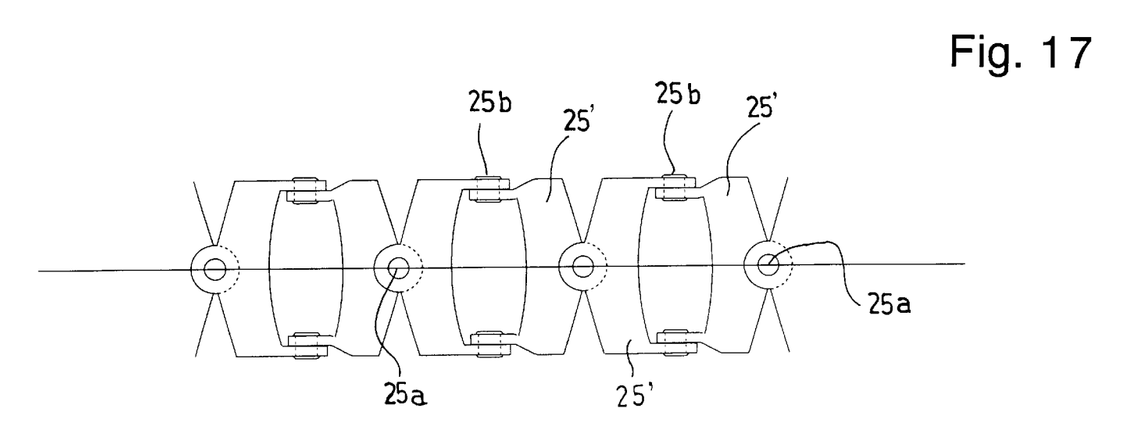
FIG. 17 is a schematic side view of part of the second embodiment of the bending portion, in the case where the bending portion is designed to be bendable in two planes perpendicular to each other.

When it is required that the bending portion 13 be bendable only in a single plane, it is sufficient that the rod-shaped endoscope body 10 be provided with the first embodiment of the bending portion 13, as shown in FIG. 16, which can bend only in a single plane. When it is required that the bending portion 13 be bendable in two planes perpendicular to each other, the bending portion 13 needs to have a structure such as shown in FIG. 17. FIG. 17 shows part of the second embodiment of the bending portion 13 in the case where the bending portion 13 is designed to be bendable in two planes perpendicular to each other. The second embodiment of the bending portion 13 is provided with an articulated series of ring joints 25'. Adjacent ring joints 25' are connected with each other by a first shaft 25a or a second shaft 25b so that each of the adjacent ring joints 25 can rotate about each of the shafts 25a and 25b. The first and second shafts 25a and 25b extend in directions perpendicular to each other and are alternately arranged. In FIG. 17 neither the steel wired tube 26 nor the aforementioned elastic covering 27 is illustrated for clarity of illustration. In the second embodiment of the bending portion 13, four bendable drive wires 20a extend within the bending portion 13 and the flexible portion 14 (see FIG. 11). The front ends of the four drive wires 20a are each secured to the hard portion 12 at 90-degree intervals about the axis of the hard portion 12. The rear ends of each pair of drive wires 20a which are diametrically opposite to each other are secured to the selective-heating device 20b. Although only two drive wires 20a are shown in FIG. 10, the remaining two drive wires 20a are provided in a similar manner in the second embodiment of the bending portion 13.

Figure 8:
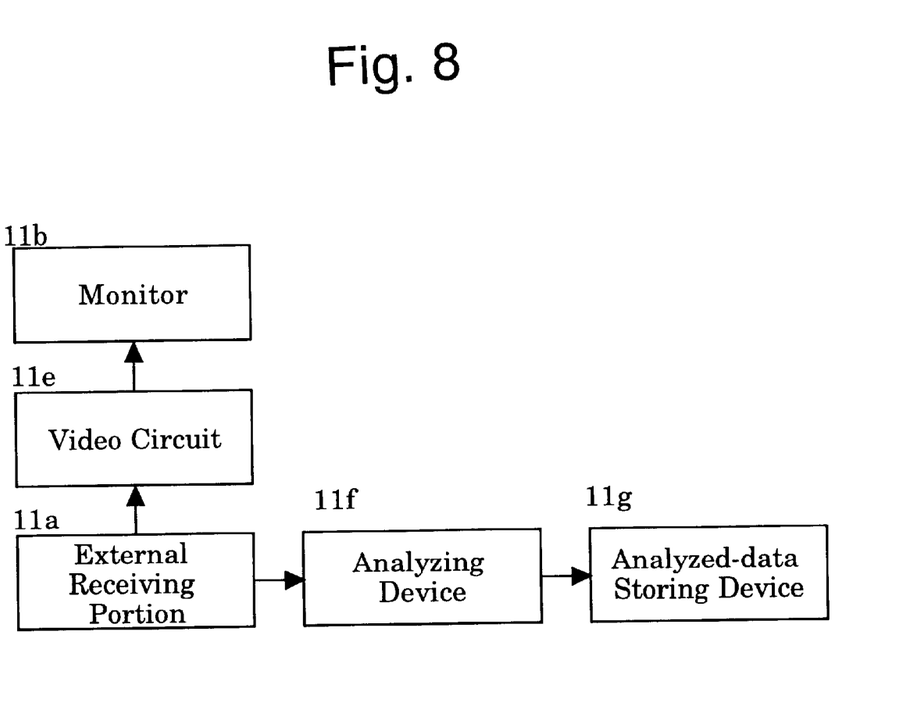
FIG. 8 is a block diagram of a process which is performed after the external device receives a signal output from the rod-shaped endoscope body.

The external device 11 shown in FIG. 1 is provided with an external receiving portion 11a, a monitor 11b, a bending portion controller portion (operational portion) 11c, an external transmitting portion 11d, a valve controlling portion 11h and a microwave transmitting portion (microwave transmitter) 11i. The external device 11 is further provided with a video circuit 11e, an analyzing device 11f and an analyzed-data storing device 11g (see FIG. 8). The external device 11 transmits the aforementioned microwave, which is used as a power supply for the rod-shaped endoscope body 10, from the microwave transmitting portion 11i to the rod-shaped endoscope body 10. This transmitted microwave is received by the microwave receiver 14h and is converted into electrical current by the power supplying device 14c. The power supplying device 14c supplies the electrical current to the transmitter/receiver device 14b and the control circuit 14d. By manually operating the bending portion controller portion 11c and the valve controlling portion 11h of the external device 11, radio operational signals for operating the bending portion 13 and the valve 14e are generated by the external device 11 to be transmitted to the rod-shaped endoscope body 10 via the external transmitting portion 11d. The external receiving portion 11a receives image signals (radio waves) transmitted from the transmitter/receiver device 14b. The received image signals are displayed on the monitor 11b to be observed by an operator.

Figure 4:
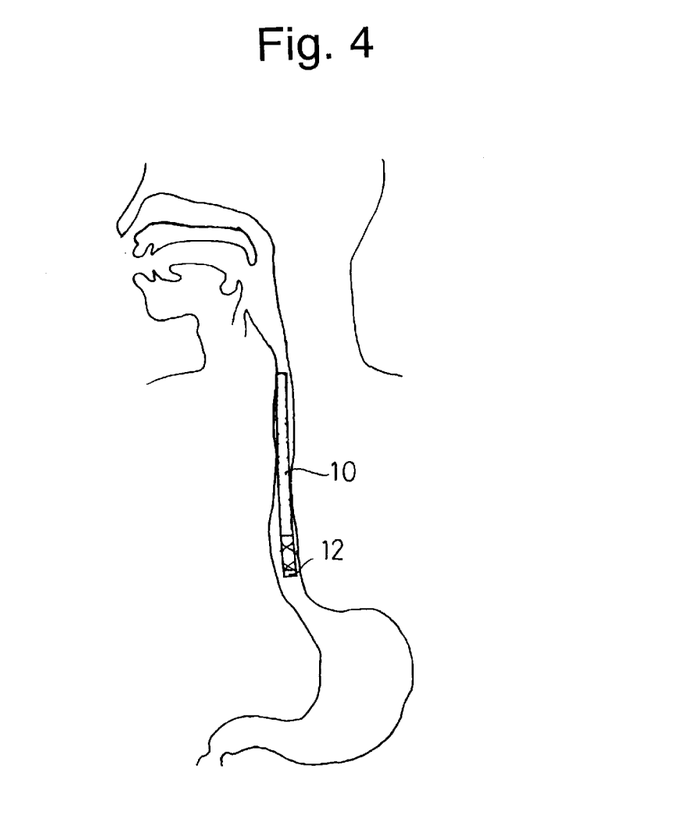
FIG. 4 is an explanatory view of the rod-shaped endoscope body shown in FIGS. 2 and 3 which is positioned in a human body, showing a state where the rod-shaped endoscope body is swallowed to reach the esophagus.
Figure 5:
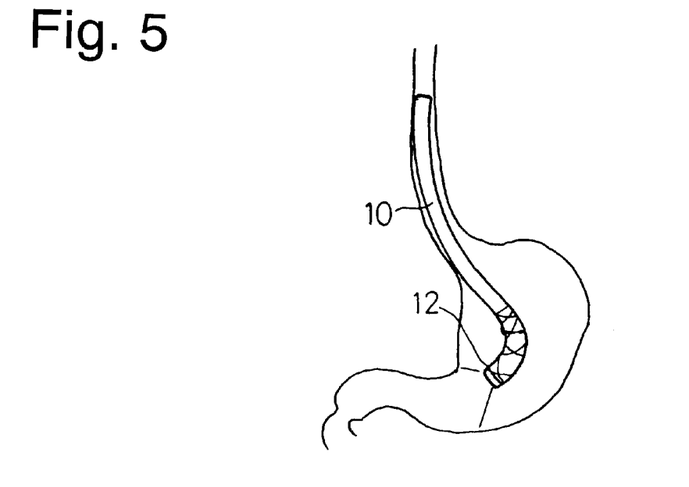
FIG. 5 is an explanatory view of the rod-shaped endoscope body shown in FIGS. 2 and 3 which is positioned between the esophagus and the stomach, showing a state where the inside of the stomach can be observed with the rod-shaped endoscope body.
Figure 6:
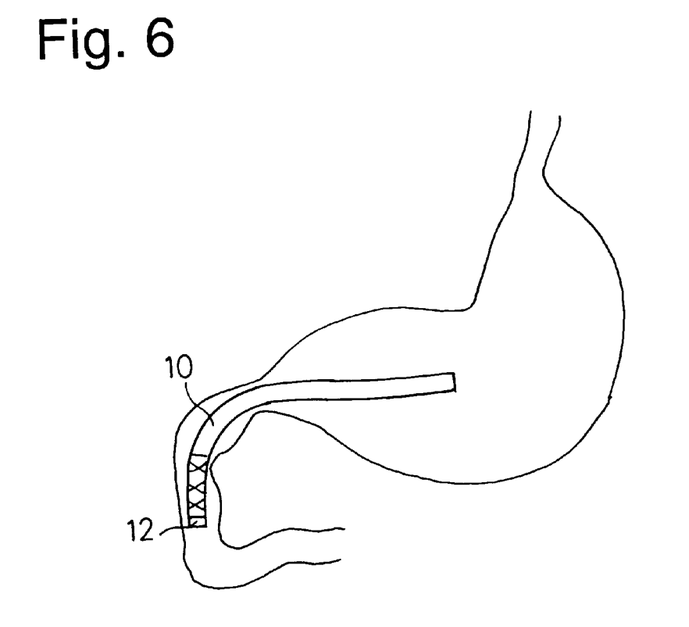
FIG. 6 is an explanatory view of the rod-shaped endoscope body shown in FIGS. 2 and 3 which is positioned between the stomach and the duodenum, showing a state where the rod-shaped endoscope body further proceeds from the stomach to the duodenum.
Figure 7:
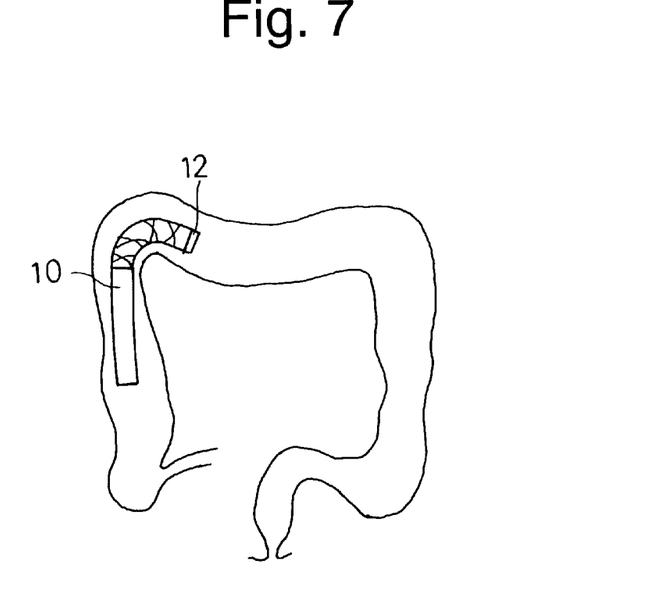
FIG. 7 is an explanatory view of the rod-shaped endoscope body shown in FIGS. 2 and 3 which is positioned in the large intestine, showing a state where the rod-shaped endoscope body proceeds within the large intestine.

In the endoscope constructed as above, a patient to be examined swallows the rod-shaped endoscope body 10 entirely from the front end thereof, i.e., from the hard portion 12. After being swallowed entirely, the rod-shaped endoscope body 10 proceeds gradually along an alimentary canal by peristalsis. FIG. 4 shows a state where the rod-shaped endoscope body 10 is swallowed to reach the esophagus. FIG. 5 shows a state where the rod-shaped endoscope body 10 is swallowed to reach the stomach, so that the inside of the stomach can be observed with the rod-shaped endoscope body 10. By proceeding further by peristalsis, the rod-shaped endoscope body 10 enters the duodenum as shown in FIG. 6. Thereafter the rod-shaped endoscope body 10 proceeds in the large intestine as shown in FIG. 7. Once the rod-shaped endoscope body 10 reaches a target inner part of the body, it can be observed via the rod-shaped endoscope body 10, and at the same time, the necessary information about a living body can be collected in a manner such as in the following description.

In the present embodiment of the endoscopic system, the transmitter/receiver device 14b of the rod-shaped endoscope body 10 receives the radio operational signals transmitted from the external transmitting portion 11d of the external device 11 so that each of the fundamental operational elements of the rod-shaped endoscope body 10 can be radio-controlled by operating the external device 11. The power supplying device 14c supplies electrical current to the transmitter/receiver device 14b and the control circuit 14d by converting the received microwave into electrical current, so that the operator does not have to care about the remaining battery power of the rod-shaped endoscope body 10. This makes it possible to observe the target inner part of the body sufficiently.

The LED 16a, which receives power from the power supplying device 14c via the signal line 18b, emits light outwardly through the illumination window 16. The object image upon which the illumination light illuminates is formed on the sensitive surface of the CCD image sensor 15b through the objective optical system 15a. The image signal supplied from the CCD image sensor 15b is amplified by the amplifier circuit 14a. This amplified image signal is transmitted from the transmitter/receiver device 14b to be subsequently received by the external receiving portion 11a of the external device 11. The image signal received by the external device 11 is processed through the video circuit 11e to be observed on the monitor 11b (see FIG. 8). The operator operates the bending portion controller portion 11c of the external device 11 to bend the bending portion 13 via the selective-heating device 20b, which is controlled by the radio operational signals transmitted from the external transmitting portion 11d, to thereby change the direction of the objective optical system 15a to observe the target inner part of the body. At this time, if an alimentary canal is made to inflate by sending the compressed air in the compressed air tank 14f from the air supply port 17 to the alimentary canal via the air supply tube 19 by operating the valve controlling portion 11h of the external device 11 so that the transmitter/receiver device 14b receives radio operational signals transmitted from the external transmitting portion 11d, so as to operate the valve 14e, the distance between the hard portion 12 and the inner space within the alimentary canal becomes large, which makes it easy to observe the inner wall of the alimentary canal.

A measuring device 24 for measuring information about a living body such as pH value, temperature, the amount of oxygen contained in blood, the hardness of the surface of cells, and the like, can be incorporated in the rod-shaped endoscope body 10 (see FIG. 3). In this case, the measured information can be transmitted from the transmitter/receiver device 14b to be received by the external receiving portion 11a of the external device 11. The received information can be analyzed and stored in the case where the analyzing device 11f analyzes the received information, and the analyzed-data storing device 11g stores the analyzed information (see FIG. 8).

Figure 9:
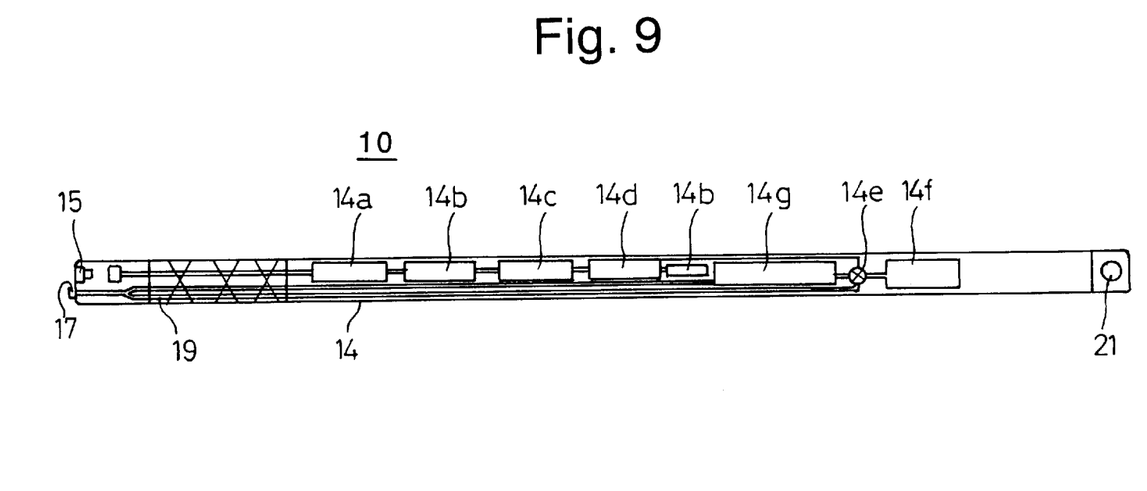
FIG. 9 is a schematic cross sectional view of the second embodiment of the rod-shaped endoscope body, according to the present invention.
Figure 15:
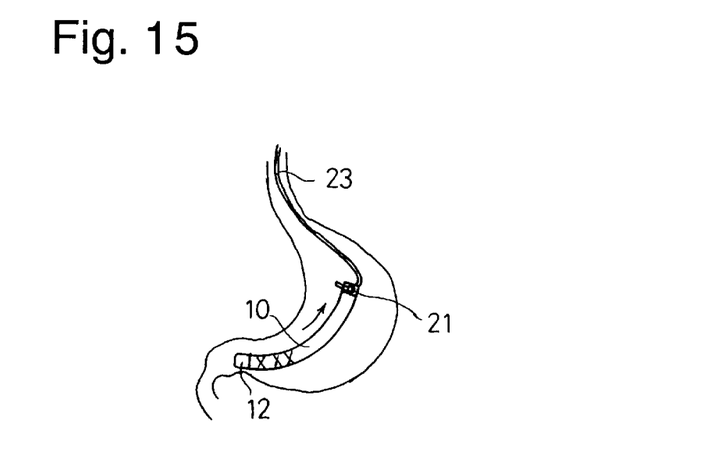
FIG. 15 is an explanatory view of the rod-shaped endoscope body shown in FIG. 9, which is positioned in the stomach, showing a state where the rod-shaped endoscope body is forcibly pulled up by a pulling device having a hook engaging with a hole formed at the rear end of the rod-shaped endoscope body.

FIG. 9 shows the second embodiment of the rod-shaped endoscope body 10 according to the present invention. In addition to the elements provided in the first embodiment of the rod-shaped endoscope body 10, the second embodiment of the rod-shaped endoscope body 10 is further provided with a water tank 14g and a hook-engaging hole 21. According to this structure, water which is loaded in the water tank 14g can be sent outwardly from the air supply port 17 via the air supply tube 19 by means of operating the valve controlling portion 11h of the external device 11 so that the transmitter/receiver device 14b receives radio operational signals transmitted from the external transmitting portion 11d, so as to operate the valve 14e. Furthermore, in the case where the operator desires to forcibly push and pull the rod-shaped endoscope body 10 positioned in a body cavity, he or she only needs to use a pulling device 23 which is provided at the distal end thereof with a hook that is engageable with the hook-engaging hole 21 (see FIG. 15). Depending upon the circumstances, the pulling device 23 can be in the form of: grasping forceps provided at the distal end thereof with a pair of claws which is used in the case where a foreign substance has to be pulled out of a body cavity of a baby or a child when he or she swallows the foreign substance, rat-teeth forceps, basket forceps used when a polyp is taken out after the polyp is cut off an inner wall of a body cavity, or forceps which are provided at the distal end thereof with a hook, etc.

Figure 12:
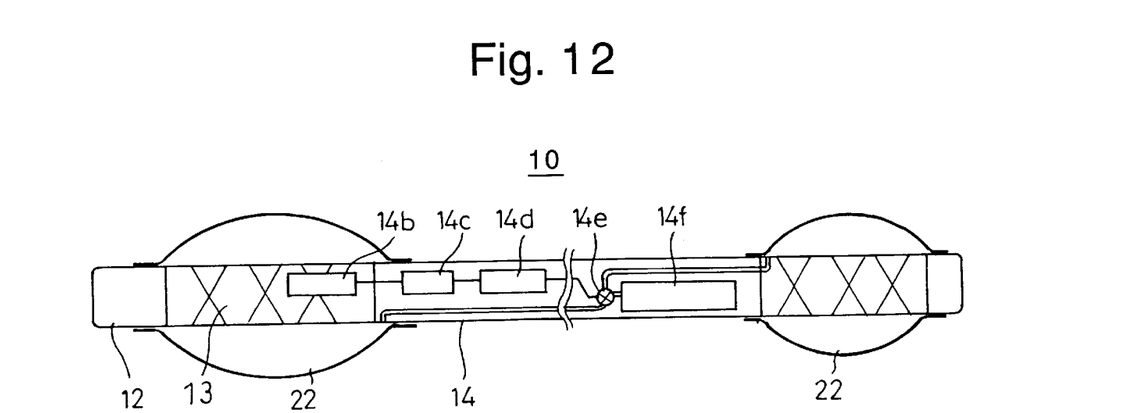
FIG. 12 is a schematic cross sectional view of the third embodiment of the rod-shaped endoscope body, according to the present invention.
Figure 13:
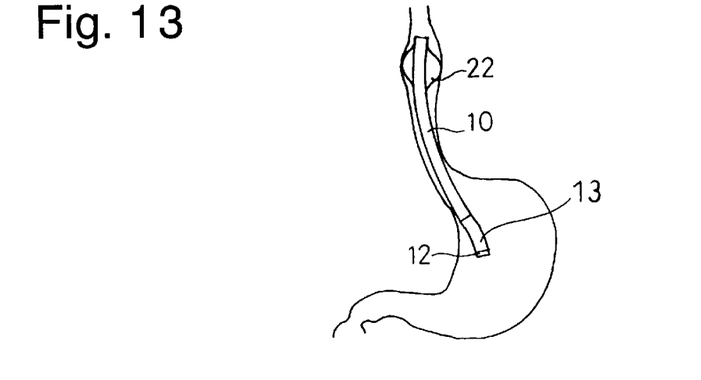
FIG. 13 is an explanatory view of the rod-shaped endoscope body shown in FIG. 12, which is positioned between the esophagus and the stomach, showing a state where the rod-shaped endoscope body is fixed to the inside of the esophagus by inflating a balloon provided at the rear end of the rod-shaped endoscope body.
Figure 14:
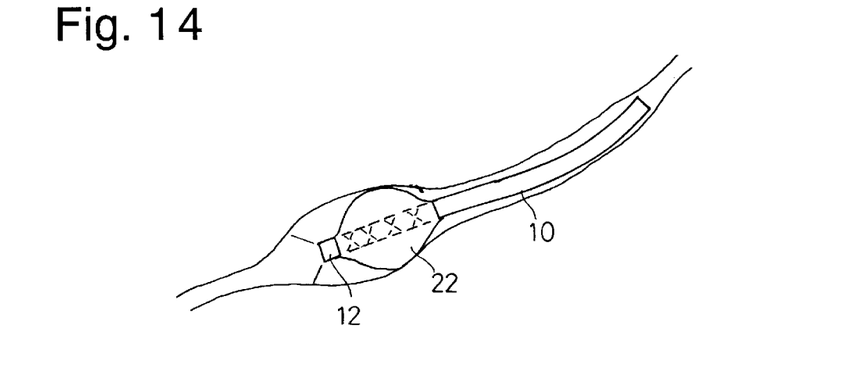
FIG. 14 is an explanatory view of the rod-shaped endoscope body shown in FIG. 12, which is positioned in an alimentary canal, showing a state where the rod-shaped endoscope body is fixed to the inner wall of the alimentary canal by inflating a balloon provided at the front end of the rod-shaped endoscope body.

FIG. 12 shows the third embodiment of the rod-shaped endoscope body 10 according to the present invention. This rod-shaped endoscope body 10 is provided with two balloons 22 respectively provided at the opposite ends of the rod-shaped endoscope body 10 as shown in FIG. 12. In an alternative, the rod-shaped endoscope body 10 can be provided with only one balloon 22 at either end. Each balloon 22 can be inflated by sending the compressed air in the compressed air tank 14f into the balloon 22, by operating the valve controlling portion 11h of the external device 11 so that the transmitter/receiver device 14b receives radio operational signals transmitted from the external transmitting portion 11d, so as to operate the valve 14e. For instance, in the case where the rod-shaped endoscope body 10 is in a tubular passage in a body, if the balloon 22 provided at the front end of the rod-shaped endoscope body 10 is inflated, the distance between the hard portion 12 and the inner wall of the tubular passage becomes large, which makes it easy to observe the inner wall of the tubular passage (see FIG. 14). Conversely, if the balloon 22 provided at the rear end of the rod-shaped endoscope body 10 is inflated, the rod-shaped endoscope body 10 can be held stably at a desired position in a case as shown in FIG. 13, the target inner portion can be easily observed by manipulating the bending portion 13.

The power supplying device 14c of the rod-shaped endoscope body 10 can be replaced by a built-in battery to simplify the structure of endoscopic system.

As can be understood from the foregoing, according to the fully-swallowable endoscopic system of the present invention, since the fully-swallowable endoscope body is entirely positioned in a body cavity without any cables or wires for connecting the rod-shaped endoscope body with any external device, a patient to be examined does not suffer from pain even if the endoscope is retained in the patient's body for a long time.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. An endoscospic system comprising:

a rod-shaped endoscope body which can be entirely swallowed by a patient to be examined so as to be located in a body cavity, at least part of said rod-shaped endoscope body comprising a bendable portion which is bendable along a curve of said body cavity; and an external device provided separately from said rod-shaped endoscope body without a mechanical connection with said rod-shaped endoscope body;

said rod-shaped endoscope body comprising a light emitter, an observing system, a transmitter for transmitting a radio wave which carries an image formed by said observing system, and a power supplying device, and said external device comprising a receiver that receives said radio wave which carries said image, said bendable portion comprising a bending portion that is configured to be bent by radio control from the external device so as to orient said light emitter and said observing system in a predetermined direction, and a flexible portion that is configured to be bent by an external force so as to bend said flexible portion along a curve of the body cavity, said bending portion being configured to be more flexible than said flexible portion.

2. The endoscopic system according to claim 1, said rod-shaped endoscope body comprising a radio-controlled driving device which receives a radio operation signal transmitted from said external device to bend said bending portion in accordance with said radio operation signal, and said external device includes an operation portion which transmits said radio operation signal to said radio-controlled driving device.

3. The endoscopic system according to claim 2, wherein said rod-shaped endoscope body further comprises a hard portion, and wherein said hard portion, said bending portion and said flexible portion are arranged in that order from one of the opposite ends of said rod-shaped endoscope body in a longitudinal direction thereof, said light emitter and said observing system being positioned in said hard portion.

4. The endoscopic system according to claim 2, wherein said radio-controlled driving device comprises a plurality of drive wires made of a shape memory alloy, and a selective-heating device which selectively heats said plurality of drive wires to bend said bending portion.

5. The endoscopic system according to claim 1, wherein said rod-shaped endoscope body further comprises a hard portion, and wherein said hard portion and said bendable portion are arranged in that order from one of the opposite ends of said rod-shaped endoscope body in a longitudinal direction thereof, said light emitter and said observing system being position in said hard portion.

6. The endoscopic system according to claim 1, wherein said power supplying device comprises a built-in battery.

7. The endoscopic system according to claim 1, wherein said external device comprises a microwave transmitter for transmitting a microwave to said rod-shaped endoscope body, and wherein said power supplying device converts said microwave into electrical current to supply the electrical current to said rod-shaped endoscope body.

8. The endoscopic system according to claim 1, wherein said observing system comprises an objective optical system and a CCD image sensor.

9. The endoscopic system according to claim 1, wherein said external device comprises a monitor which visually indicated said image.

10. The endoscopic system according to claim 1, said flexible portion being bendable along a curve of the body cavity independently of said external device.

11. An endoscopic system comprising:

a rod-shaped endoscope body which comprises a hard portion, a bending portion and a flexible portion which are arranged in that order; and a radio controller for manipulating said bending portion so as to bend by radio-control, said rod-shaped endoscope body comprising a light emitter that illuminates a target inner portion of a living body;

an image pick-up device that takes an image of said target inner portion illuminated by said light emitter; and a transmitter that transmits a radio wave which carries said image taken by said image pick-up device, said bending portion being configured to be bent by radio control from the external device so as to orient said light emitter and said observing system in a predetermined direction, said flexible portion being configured to be bent by an external force so as to bend said flexible portion along a curve of the body cavity, said bending portion being configured to be more flexible than said flexible portion.

12. The endoscopic system according to claim 11, wherein said radio controller comprises a monitor and a receiver, for receiving said radio wave, wherein said image is indicated on said monitor.

13. The endoscopic system according to claim 11, wherein said radio controller further comprises a second transmitter for transmitting a microwave to said rod-shaped endoscope body, and wherein said rod-shaped endoscope body is provided therein with a power supplying device which receives said microwave to convert said microwave into electrical current which is to be used as a power source of said rod-shaped endoscope body.

14. The endoscopic system according to claim 11, said bending portion comprising a plurality of adjacently positioned articulated joints.

15. The endoscopic system according to claim 11, said flexible portion being bendable along a curve of the body cavity independently of said external device.

16. An endoscope system comprising:

a rod-shaped endoscope body which can be swallowed by a patient to be examined so as to be located in a body cavity, at least part of said rod-shaped endoscope body comprising a bendable portion which is bendable along a curve of said body cavity;

said rod-shaped endoscope body comprising a light emitter, an observing system, a transmitter that transmits to an external device, a radio wave which carries an image formed by said observing system, and a power supplying device, said bendable portion comprising:

a bending portion configured to be bent by radio control from the external device to orient the light emitter and observing system in a predetermined direction; and a flexible portion configured to be bent when an external force is applied to said flexible portion so as to bend along a curve of the body cavity, said bending portion being configured to be more flexible than said flexible portion;

said rod-shaped endoscope body comprising a radio-controlled driving device which receives a radio operation signal transmitted from the external device to bend said bending portion in accordance with the radio operation signal.

17. The endoscopic system according to claim 1, said bending portion comprising a plurality of adjacently positioned articulated joints.

18. The endoscope system according to claim 16, said flexible portion being bendable along a curve of the body cavity independently of a signal received by said driving device.

* * * * *